US010434089B2

(12) United States Patent
Lamichhane

(10) Patent No.: US 10,434,089 B2
(45) Date of Patent: Oct. 8, 2019

(54) AVIBACTAM AND CARBAPENEMS ANTIBACTERIAL AGENTS

(71) Applicant: THE JOHNS HOPKINS UNIVERSITY, Baltimore, MD (US)

(72) Inventor: Gyanu Lamichhane, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/877,762

(22) Filed: Jan. 23, 2018

(65) Prior Publication Data

US 2018/0207142 A1 Jul. 26, 2018

Related U.S. Application Data

(60) Provisional application No. 62/450,295, filed on Jan. 25, 2017.

(51) Int. Cl.
  *A61K 31/439* (2006.01)
  *A61P 31/04* (2006.01)
  *A61K 31/407* (2006.01)

(52) U.S. Cl.
  CPC .......... *A61K 31/439* (2013.01); *A61K 31/407* (2013.01); *A61P 31/04* (2018.01)

(58) Field of Classification Search
  CPC .................................................. A61K 31/439
  See application file for complete search history.

(56) References Cited

U.S. PATENT DOCUMENTS

| | | | |
|---|---|---|---|
| 5,399,363 A | 3/1995 | Liversidge et al. |
| 5,466,468 A | 11/1995 | Schneider et al. |
| 5,543,158 A | 8/1996 | Gref et al. |
| 5,580,579 A | 12/1996 | Ruddy et al. |
| 5,629,001 A | 5/1997 | Michael et al. |
| 5,641,515 A | 6/1997 | Ramtoola |
| 5,725,871 A | 3/1998 | Illum |
| 5,756,353 A | 5/1998 | Debs |
| 5,780,045 A | 7/1998 | McQuinn et al. |
| 5,792,451 A | 8/1998 | Sarubbi et al. |
| 5,804,212 A | 9/1998 | Illum |
| 6,613,308 B2 | 9/2003 | Bartus et al. |
| 8,829,191 B2 | 9/2014 | Ronsheim et al. |
| 2016/0348187 A1 | 12/2016 | Rey et al. |

FOREIGN PATENT DOCUMENTS

| | | |
|---|---|---|
| WO | 2012079504 A1 | 6/2012 |
| WO | 2014135930 A1 | 3/2013 |
| WO | 2013121279 A2 | 8/2013 |
| WO | 2015087245 A1 | 12/2013 |
| WO | 2014122468 A1 | 8/2014 |
| WO | 2015145161 A1 | 10/2015 |
| WO | 2017008034 A1 | 1/2017 |
| WO | WO-2017008034 A1 * | 1/2017 ............ A61K 45/06 |

OTHER PUBLICATIONS

Kaushik et al., Carbapenems and Rifampin Exhibit Synergy against *Mycobacterium tuberculosis* and *Mycobacterium abscessus*, Antimicrob Agents Chemother., Oct. 2015; 59(10):6561-7.*
VanScoy et al., Pharmacokinetics-pharmacodynamics of a novel β-lactamase inhibitor, CB-618, in combination with meropenem in an in vitro infection model, Antimicrobial Agents and Chemotherapy (2016), 60(7), 3891-3896.*
Mavridou et al., Pharmacodynamics of imipenem in combination with β-lactamase inhibitor MK7655 in a murine thigh model, Antimicrobial Agents and Chemotherapy (2015), 59(2), 790-795.*
Dubee, β-Lactamase inhibition by avibactam in *Mycobacterium abscessus*, Journal of Antimicrobial Chemotherapy, vol. 70, Issue 4, Apr. 1, 2015, pp. 1051-1058.*
Jonsson, et al., Molecular epidemiology of *Mycobacterium abscessus*, with focus on cystic fibrosis. J Clin Microbiol. May 2007;45(5):1497-504.
Martiniano, et al., Nontuberculous Mycobacterial Infections in Cystic Fibrosis. Clin Chest Med. Mar. 2016;37(1):83-96.
Olivier, et al., Nontuberculous mycobacteria. I: multicenter prevalence study in cystic fibrosis. Am J Respir Crit Care Med. Mar. 15, 2003;167(6):828-34.
Prevots, et al., Nontuberculous mycobacterial lung disease prevalence at four integrated health care delivery systems. Am J Respir Crit Care Med. Oct. 1, 2010;182(7):970-6.
Griffith, et al., An official ATS/IDSA statement: diagnosis, treatment, and prevention of nontuberculous mycobacterial diseases. Am J Respir Crit Care Med. Feb. 15, 2007;175(4):367-416.
Nessar, et al., *Mycobacterium abscessus*: a new antibiotic nightmare. J Antimicrob Chemother. Apr. 2012;67(4):810-8.
Lavollay, et al., The Peptidoglycan of *Mycobacterium abscessus* is Predominantly Cross-Linked by I,d-Transpeptidases. J Bacteriol. Feb. 2011; 193(3): 778-782.
Dubee, et al., Inactivation of *Mycobacterium tuberculosis* I,d-transpeptidase LdtMt, by carbapenems and cephalosporins. Antimicrob Agents Chemother. Aug. 2012;56(8):4189-95.
Cordillot, et al., In vitro cross-linking of *Mycobacterium tuberculosis* peptidoglycan by L,D-transpeptidases and inactivation of these enzymes by carbapenems. Antimicrob Agents Chemother. Dec. 2013;57(12):5940-5.
Lavollay, et al., In vitro activity of cefoxitin and imipenem against *Mycobacterium abscessus* complex. Clin Microbiol Infect. May 2014;20(5):297-300.
Soroka, et al., Characterization of broad-spectrum *Mycobacterium abscessus* class A β-lactamase. J Antimicrob Chemother. Mar. 2014;69(3):691-6.
Lefebvre, et al., Bactericidal and intracellular activity of β-lactams against *Mycobacterium abscessus*. J Antimicrob Chemother. Jun. 2016;71(6):1556-63.

(Continued)

*Primary Examiner* — Svetlana M Ivanova
(74) *Attorney, Agent, or Firm* — Johns Hopkins Tech Ventures

(57) ABSTRACT

Described are methods of treating or preventing a bacterial infection by administering an antibacterial agent comprising a β-lactamase inhibitor and one or more carbapenem to a subject.

13 Claims, 2 Drawing Sheets

(56) References Cited

OTHER PUBLICATIONS

Dubee, et al., β-Lactamase inhibition by avibactam in *Mycobacterium abscessus*. J Antimicrob Chemother. Apr. 2015;70(4):1051-8.

Soroka, et al., Inhibition of β-lactamases of mycobacteria by avibactam and clavulanate. J Antimicrob Chemother. Apr. 1, 2017;72(4):1081-1088.

Gavan, et al., A microdilution method for antibiotic susceptibility testing: an evaluation. Am J Clin Pathol. Jun. 1970;53(6):880-5.

Nix, et al., Pharmacokinetics and pharmacodynamics of ertapenem: an overview for clinicians. J Antimicrob Chemother. Jun. 2004;53 Suppl 2:ii23-8.

Wallace, et al., Treatment of nonpulmonary infections due to *Mycobacterium fortuitum* and *Mycobacterium chelonei* on the basis of in vitro susceptibilities. J Infect Dis. Sep. 1985;152(3):500-14.

Wright, Empowering Older Antibiotics. Cell. 2016;167(2):301.

Wang, et al., The road to avibactam: the first clinically useful non-β-lactam working somewhat like a β-lactam. Future Med Chem. Jun. 2016;8(10):1063-84.

Humphres, et al., First Report of Ceftazidime-Avibactam Resistance in a KPC-3-Expressing Klebsiella pneumoniae Isolate. Antimicrob Agents Chemother. Oct. 2015;59(10):6605-7.

Morrill, et al., Treatment Options for Carbapenem-Resistant Enterobacteriaceae Infections. Open Forum Infect Dis. Apr. 2015; 2(2): ofv050.

Ito, et al., [Activity of cephems and carbapenems against clinically isolated Mycobacterium abscessus]. Kekkaku. Sep. 2003;78(9):587-90.

Kumar, et al., Non-classical transpeptidases yield insight into new antibacterials. Nat Chem Biol. Jan. 2017;13 (1):54-61.

Winthrop, et al., Pulmonary nontuberculous mycobacterial disease prevalence and clinical features: an emerging public health disease. Am J Respir Crit Care Med. Oct. 1, 2010;182(7):977-82.

Goa, K., et al., "Panipenem/Betamipron" Drugs 2003; 63 (9): 913-925.

* cited by examiner

FIG. 2

AVIBACTAM AND CARBAPENEMS ANTIBACTERIAL AGENTS

REFERENCE TO RELATED APPLICATIONS

This application claims the benefit of U.S. Provisional Patent application 62/450,295 filed Jan. 25, 2017, which is hereby incorporated by reference for all purposes as if fully set forth herein.

STATEMENT OF GOVERNMENTAL INTEREST

This invention was made with government support under grant no. R21AI121805 awarded by the National Institutes of Health. The government has certain rights in the invention.

BACKGROUND OF THE INVENTION

*Mycobacterium abscessus* is a rapidly growing non-tuberculous *mycobacterium* (NTM) found widely in soil and water and can cause a spectrum of infections. Prevalence of *M. abscessus* infections in the lungs of people with chronic conditions such as cystic fibrosis is significant and can often lead to serious morbidity and mortality. A survey revealed that *M. abscessus* is present in the sputum of ~13% of cystic fibrosis patients in the US. Among NTM lung infections, *M. abscessus* is one of the prevalent species and often leads to a chronic and incurable disease. Drug resistance in *M. abscessus* is steadily rising globally making it increasingly difficult to manage infections with these strains. Therefore, new drugs and novel regimens are acutely needed to treat infections with *M. abscessus*. An ideal new drug would inhibit a novel target so that it can be effective against *M. abscessus* strains that are resistant to currently used drugs.

SUMMARY OF THE INVENTION

One embodiment of the present invention is a method of treating or preventing a bacterial infection comprising the following steps: administering an agent comprising a β-lactamase inhibitor and one or more carbapenem to a subject and treating or preventing a bacterial infection in the subject. Examples of suitable carbapenems used in the present invention includes ertapenem, meropenem, imipenem, doripenem, biapenem, faropenem, tebipenem, panipenem and a combination thereof. Examples of suitable β-lactamase inhibitors used in the present invention includes is avibactam or clavulanate, or a combination thereof. Within a method of the present invention the treating of bacterial infection occurs when at least one symptom of the bacterial infection is alleviated compared to a reference subject that was not been administered the agent. A preferred β-lactamase inhibitor is avibactam especially when treating a *Mycobacterium abscessus* infection. An example of a suitable amount of β-lactamase inhibitor that may be used in the present invention include an amount that is sufficient of to reduce the minimum inhibitory concentration of the one or more carbapenem in the range of 2 to 32 fold; that is sufficient to reduce the minimum inhibitory concentration of the one or more carbapenems by greater or equal to 2-fold; that is sufficient to reduce the minimum inhibitory concentration of the one or more carbapenems by greater or equal to 3-fold; that is sufficient to reduce the minimum inhibitory concentration of one or more carbapenems by greater or equal to 5-fold; that is sufficient to reduce the minimum inhibitory concentration of one or more carbapenems by greater or equal to 8-fold; that is sufficient to reduce the minimum inhibitory concentration of one or more carbapenems by greater or equal to 13-fold; or that is sufficient to reduce the minimum inhibitory concentration of one or more carbapenems by greater or equal to 38-fold and bring it to therapeutically usable doses. Alternatively, the one or more carbapenem is selected from the group consisting of tebipenem, ertapenem, and panipenem.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "analog" is meant a molecule that is not identical, but has analogous functional or structural features.

By "disease" is meant any condition or disorder that damages or interferes with the normal function of a cell, tissue, or organ. Examples of diseases include a bacterial infection.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "reduces" is meant a negative alteration.

A "reference" refers to a standard or control conditions such as a sample (human cells) or a subject that is a free, or substantially free, of an agent such as one or more agents of the present invention comprising a β-lactamase inhibitor and a carbapenem.

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

BRIEF DESCRIPTION OF THE DRAWINGS

FIG. 2 illustrates Table 2: Antimicrobial susceptibility profiles of twenty eight *M. abscessus* clinical strains against carbapenems (with and without avibactam, 4 µg/mL) and antibacterials that are currently used to treat *M. abscessus* infection and where available currently used CLSI breakpoints for interpretation. CLR, clarithromycin (susceptible, 0.06 µg/mL to 2 µg/mL, intermediate, 4 µg/mL, resistant, ≥8 µg/mL); SXT, trimethoprim/sulfamethoxazole (susceptible, 0.25/4.75 to 2/38 µg/mL, resistant, ≥4/76 µg/mL); CIP, ciprofloxacin (susceptible, 0.12 µg/mL to 1 µg/mL, intermediate, 2 µg/mL, resistant, ≥4 µg/mL); MXF, moxifloxacin (susceptible, 0.25 µg/mL to 1 µg/mL, intermediate, 2 µg/mL, resistant, ≥4 µg/mL); FOX, cefoxitin (susceptible, 4 µg/mL to 16 µg/mL, intermediate, 32-64 µg/mL, resistant, ≥128 µg/mL); AMI, amikacin (susceptible, 1 µg/mL to 16 µg/mL, intermediate, 32 µg/mL, resistant, ≥64 µg/mL); TGC, tigecycline (no interpretation for this drug currently available, however an MIC>4 µg/mL for *M. tuberculosis* is considered resistant in broth); LZD, linezolid (susceptible, 1 µg/mL to 8 µg/mL, intermediate, 16 µg/mL, resistant, ≥32 µg/mL); IMI, imipenem (susceptible, 2 µg/mL to 4 µg/mL, intermediate, 8 µg/mL to 16 µg/mL, resistant, ≥32 µg/mL); TOB, tobramycin (susceptible, 1 µg/mL to 2 µg/mL, intermediate, 4 µg/mL, resistant, ≥8 µg/mL); KAN, kanamycin (no interpretation for this drug currently available, however, an MIC>5 µg/ml for *M. tuberculosis* is considered resistant in broth; Tebipenem (Tebi), ertapenem (Erta), panipenem (Pani), doripenem (Dori), biapenem (Bia), meropenem (Mero), faropenem (Faro), imipenem (Imi), avibactam (Avi) and not determined (ND).

DETAILED DESCRIPTION OF THE INVENTION

Figure 1:
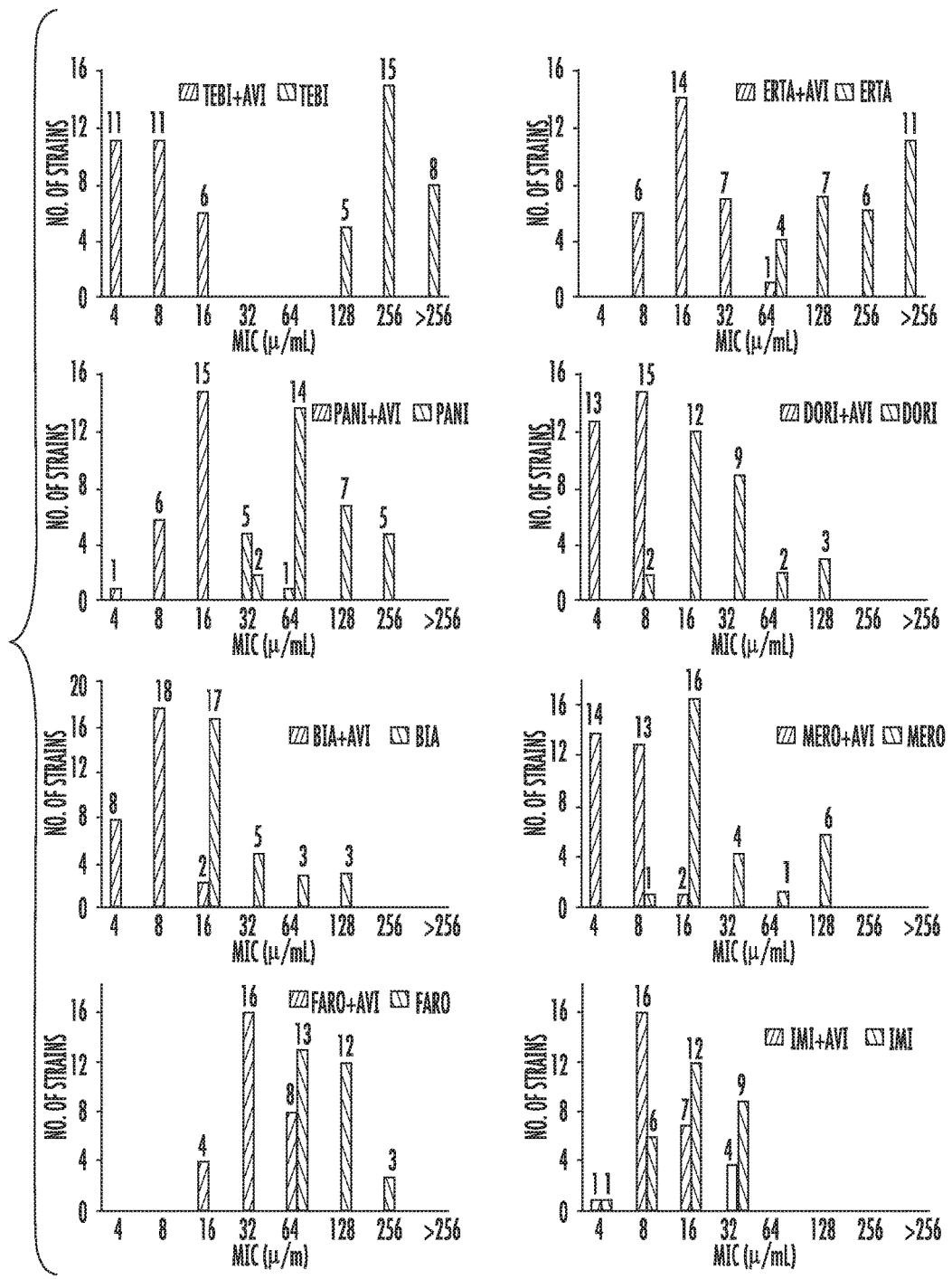
FIG. 1 illustrates the distribution of susceptibility of *M. abscessus* strains (n=28) against carbapenems with or without 4 µg/mL avibactam (Avi). The data labels in each plot represent the number of isolates. Tebipenem (Tebi), ertapenem (Erta), panipenem (Pani), doripenem (Dori), biapenem (Bia), meropenem (Mero), faropenem (Faro) and imipenem (Imi).

The peptidoglycan is an Achilles's heel of bacteria as agents that inhibit its biosynthesis, namely β-lactams and glycopeptides, comprise some of the most widely used class of antibacterials in modern medicine. β-lactams derive their activity by preventing formation of linkage between peptide sidechains by inhibiting the transpeptidases that catalyze this reaction. Recently it was demonstrated that majority of the linkages in the peptidoglycan layer of *M. abscessus* are generated by LD-transpeptidases and that this class of enzyme is selectively more susceptible to the carbapenem class of β-lactams. Imipenem, a carbapenem, has superior activity compared to cefoxitin against clinical strains of *M. abscessus* isolated from cystic fibrosis patients. *M. abscessus* harbors a chromosomally encoded β-lactamase that is highly active and therefore is of major concern while considering β-lactams for treatment of *M. abscessus* infections. Here, we have studied if avibactam, a recently developed β-lactamase inhibitor, can alter the potency of the carbapenem class of β-lactams against *M. abscessus*. Recent studies have provided insight into the activities of some older carbpenems with or without avibactam against *M. abscessus*. We have included all commercially available carbapenems, most importantly new and oral carbapenems, and a collection of clinically isolated *M. abscessus* strains most of which are resistant to multiple drugs currently deployed to treat infection by this pathogen. Activities of the combinations of clavulanate, a β-lactamase inhibitor, and carbapenems, were recently reported; therefore clavulanate was excluded from this study.

Bacterial Strains

Twenty eight unique clinical isolates of *M. abscessus* were used in this study. These strains were obtained de-identified from the archive of the clinical microbiology laboratory of the Johns Hopkins University Hospital per institutional ethical guidelines. They were isolated over a 10 year period, from 2005-2015, from patients that were temporally and geographically unrelated. No two isolates are from the same patient. Those displaying a high level of resistance to antibacterials used for *M. abscessus* infection were selected for this study. All strains obtained prior to 2014 were identified to the *M. abscessus* complex level using a variety of methods including 16S rDNA sequencing in conjunction with selected biochemical testing such as sodium citrate. More recent isolates (those isolated after 2014) were identified using MALDI ToF mass spectrometry in which a Bruker MicroFlex LT (MicroFlex LT) mass spectrometer and Bruker Biotyper software and existing database (version 2.0, Bruker) were employed. Sub-speciation within the *M. abscessus* complex, which helps to distinguish between *M. abscessus* sensu stricto, *M. massiliense*, and *M. bolletii*, was not done as this is not per the current standard of care at the Johns Hopkins Clinical Mycobacteriology Laboratory. Distinguishing between *M. abscessus* sensu stricto and *M. massiliense* is most often performed to guide therapy since *M. massiliense* is known to have a non-functional erm gene and is therefore susceptible to macrolides. However, due to the high number of macrolide resistant *M. abscessus* complex isolates recovered at Johns Hopkins, most patient isolates are subjected to drug susceptibility testing, making speciation within the complex of lesser importance. Thus, the proportion of each subspecies within the M. abscessus complex for the Johns Hopkins strain collection is not known. M. abscessus ATCC 19977 was included as a reference drug-sensitive strain.

ence of the aforementioned four β-lactamase inhibitors. In general, addition of sulbactam and tazobactam failed to reduce the MICs of the carbapenems (Table 1). However, avibactam (4 µg/mL) consistently reduced the MICs of carbapenems by 2 to 32 fold. Based on these data, we selected avibactam for further consideration.

TABLE 1

Minimum inhibitory concentrations (in µg/mL) of carbapenems with and without β-lactamase inhibitors against M. abscessus ATCC 19977. β-lactamase inhibitors sulbactam, tazobactam and avibactam were used at a fixed concentration of 4 µg/mL. Cation-adjusted Mueller-Hinton broth (CAMHB), not determined (ND).

| Drug | 7H9 broth | 7H9 + sulbactam | 7H9 + tazobactam | 7H9 + avibactam | CAMHB only | CAMHB + avibactam |
|---|---|---|---|---|---|---|
| Ertapenem | 64-128 | >64 | 32-64 | 4-8 | 128-256 | 8-16 |
| Meropenem | 8-16 | 8-16 | 8-16 | 2-4 | 32-64 | 4-8 |
| Imipenem | 4-8 | 4-8 | 2-4 | 2-4 | 8-16 | 4-8 |
| Doripenem | 8-16 | 8-16 | 8-16 | 2-4 | 16-32 | 4-8 |
| Biapenem | 8-16 | 4-8 | 8-16 | 2-4 | 16-32 | 8-16 |
| Faropenem | 32-64 | 16-32 | 32-64 | 8-16 | 64-128 | 16-32 |
| Tebipenem | 128-256 | >64 | >64 | 4-8 | 128-256 | 8-16 |
| Panipenem | 64-128 | 16-32 | 32-64 | 8-16 | 64-128 | 8-16 |
| Sulbactam | >64 | ND | ND | ND | ND | ND |
| Tazobactam | >64 | ND | ND | ND | ND | ND |
| Avibactam | >256 | ND | ND | ND | >256 | ND |

Growth Conditions and Minimum Inhibitory Concentration (MIC)

All strains were initially grown in 7H9 complete medium composed of Middlebrook 7H9 broth (Difco) supplemented with 0.5% glycerol, 10% oleic acid-albumin-dextrose-catalase and 0.05% Tween-80 at 37° C. with constant shaking. A standard broth microdilution method [20] was used to determine MIC. Briefly, M. abscessus strains were grown as described above and these cultures, at exponential phase ($A_{600\ nm}$~0.6-0.8), were used to inoculate $10^5$ colony forming units (CFU) into each well of microtiter culture plates containing a carbapenem at two fold serial dilutions ranging from 256 to 0.25 µg/mL. An identical setup but with wells containing 4 µg/mL of avibactam was used to assess the effect of this agent on each carbapenem. Carbapenems studied were procured commercially from Sigma-Aldrich and include ertapenem, meropenem, imipenem, doripenem, biapenem, faropenem, tebipenem and panipenem. β-lactamase inhibitors sulbactam, tazobactam and avibactam were also procured from Sigma-Aldrich. In addition, to establish baseline antibacterial susceptibility for each strain we also determined MICs for drugs currently used to treat M. abscessus infections. They are linezolid, cefoxitin, kanamycin, ciprofloxacin, moxifloxacin, amikacin, tigecycline, imipenem, tobramycin, trimethoprim/sulfamethoxazole, and clarithromycin. M. abscessus growth was evaluated by visual inspection of pellets after 3 days of incubation (the exception being clarithromycin for which incubation was extended to 14 days) at 30° C. without shaking per CLSI guidelines [21]. In addition to assessment in 7H9 complete medium, we also used cation adjusted Mueller-Hinton broth for MIC studies for the reference strain M. abscessus ATCC 19977. All experiments were repeated and the final data represent the average of two biological replicates.

Figure 2:
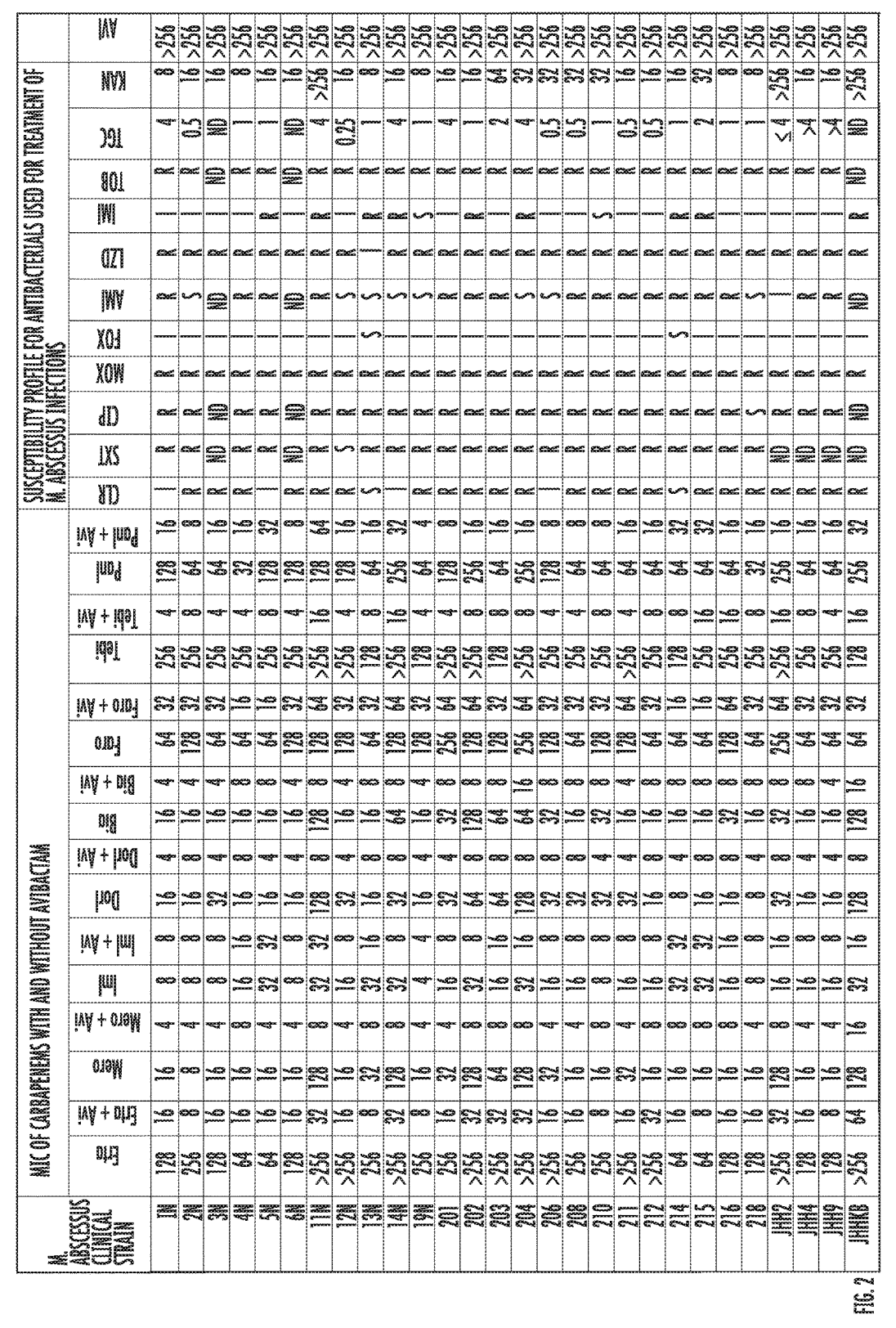

We studied the utility of β-lactamase inhibitors sulbactam, tazobactam, and avibactam in restoring in vitro potencies of carbapenems against M. abscessus using the reference drug-susceptible strain ATCC 19977. We determined MICs of ertapenem, meropenem, imipenem, doripenem, biapenem, faropenem, tebipenem and panipenem alone or in the pres- The twenty eight clinical isolates included in this study exhibited a wide range of susceptibilities and resistance to the antibacterials used to treat M. abscessus infections (FIG. 2 of Table 2). This baseline profile illustrates that these clinical isolates are mostly resistant to the drugs that are part of the current recommendation for treatment of M. abscessus infections, with tigecycline being the only exception. The MIC of carbapenems against the drug sensitive control strain M. abscessus ATCC 19977 were as expected. They were 128, 16, 8, 16, 16, 64, 256 and 128 µg/mL for ertapenem, meropenem, imipenem, doripenem, biapenem, faropenem, tebipenem and panipenem, respectively. Broth microdilution breakpoints for imipenem and meropenem have been established for rapidly-growing mycobacteria, including M. abscessus and are the same for both drugs: susceptible, ≤4 µg/mL, intermediate 8 µg/mL to 16 µg/mL, and resistant ≥32 µg/mL. However, breakpoints for M. abscessus have not been established for any of the other carbapenems tested in this study. In such cases, comparison of individual MICs to average peak plasma level and half-life may be useful clinically (ertapenem: average peak plasma concentration ~150 µg/mL with a half-life of ~4 hrs; tebipenem: average peak plasma concentration ~8 µg/mL with a half-life of 1 hr; panipenem: average peak plasma concentration ~22 µg/mL with a half-life of 40 to 70 minutes).

Compared to ATCC 19977, the twenty eight clinical isolates were equally or more resistant to the carbapenems with a few exceptions (FIG. 2 of Table 2). The average reduction in MICs of the carbapenems, in combination with avibactam, against the twenty eight clinical strains is as follows: imipenem (2 fold), faropenem (3 fold), biapenem (5 fold), doripenem (6 fold), meropenem (6 fold), panipenem (8 fold), ertapenem (>13 fold) and tebipenem (>38 fold) (FIG. 1). While avibactam was least effective in reducing the MICs of imipenem and faropenem against M. abscessus it was able to restore the MICs of panipenem, ertapenem and tebipenem to levels that are therapeutically relevant. These data also show an interesting pattern: irrespective of how high or low the MIC of a carbapenem alone, avibactam can reduce the final MIC to no lower than 4-8 µg/mL. Therefore, it appears that there is a lower limit for MIC of carbapenem and avibactam combination.

Discussion

*M. abscessus* is considered to be the most virulent of the rapidly growing mycobacteria. This organism most commonly affects immunocompromised hosts; for example, those with cystic fibrosis and lung transplant recipients, and is largely considered to be a chronic and incurable disease. Effective antimicrobial treatment is sometimes the only thing that stands between these patients and overwhelming infection or even death.

The treatment regimen for *M. abscessus* pulmonary disease generally involves combination therapy with multiple agents for an extended course of several months. Many of these antibiotics are poorly-tolerated and are associated with significant cytotoxic effects. The high prevalence of both intrinsic and acquired antimicrobial resistance further complicates this regimen, making development of novel treatment strategies crucial. *M. abscessus* genome encodes a β-lactamase, $Bla_{Mab}$, which is not effectively inhibited by clavulanate, sulbactam and tazobactam. We have also failed to observe significant reduction in MIC of carbapenems against *M. abscessus* when supplemented with clavulanate or sulbactam or tazobactam (Table 1). $Bla_{Mab}$ has been shown to hydrolyze β-lactams with high efficiency, especially imipenem. While this study suggested that avibactam could potentially protect imipenem from $Bla_{Mab}$, in our study, the MIC of imipenem was least altered by avibactam (FIG. 1 and FIG. 2 of Table 2). Therefore, it appears that *M. abscessus* likely possess an additional way to degrade imipenem even when it is protected from $Bla_{Mab}$ by avibactam. On the other hand, it is plausible that tebipenem, ertapenem and panipenem are efficiently hydrolyzed by $Bla_{Mab}$ and any additional mechanism present in *M. abscessus*, and avibactam effectively protects these carbapenems.

Our study showed that the addition of avibactam to various carbapenem antibiotics effectively reduced the MICs of carbapenem-resistant *M. abscessus* isolates to within therapeutically-achievable levels in vitro. Additionally, the largest reduction in MIC was achieved with tebipenem, which is available in an oral formulation and may further simplify the multi-drug treatment regimen.

Both carbapenems and β-lactamase inhibitors are FDA approved, widely available, and generally well-tolerated. The results of our study are highly promising, as they denote a potential new treatment strategy for carbapenem-resistant *M. abscessus* that could be easily implemented in clinical practice.

Avibactam is the most active β-lactamase inhibitor in reducing the MICs of tebipenem, ertapenem and panipenem; if it were not for avibactam, the MIC of these carbapenems would be well outside the clinically relevant therapeutic window. For those carbapenems that exhibit high MIC against *M. abscessus*, addition of avibactam usually reduces the MIC. However, it appears that avibactam reduces the MIC to 2-8 µg/mL, but not below this range, irrespective of how high the MIC of a carbapenem alone is.

The present invention determined that avibactam can restore potency of carbapenems against *M. abscessus*. Using a full panel of carbapenems against a collection of independent *M. abscessus* clinical isolates, the inventors observed that for select carbapenems, avibactam greatly reduces their MIC. Avibactam reduces the MIC of tebipenem against *M. abscessus* to 4-8 µg/mL, representing a 32-64 fold decrease. This concentration is achievable in the blood making tebipenem-avibactam combination a potentially new regimen for treatment of *M. abscessus* infection. Avibactam also reduces the MIC of ertapenem and panipenem against *M. abscessus* to levels achievable in the blood.

Embodiments of the disclosure concern methods and/or compositions for treating and/or preventing a bacterial infection. In certain embodiments, individuals with a bacterial infection are treated with an agent comprising a β-lactamase inhibitor and a carbapenem of the present invention wherein the β-lactamase inhibitor reduces the minimum inhibitory concentration of one or more carbpenem in the range of 2 to 32 fold, or any of the ranges described in this specification.

In certain embodiments, the level to which a β-lactamase inhibitor reduces the minimum inhibitory concentration of one or more carbpenem may be any level so long as it provides amelioration of at least one symptom of the bacterial infection. The β-lactamase inhibitor may reduce the minimum inhibitory concentration of one or more carbpenem by at least 2, 3, 4, 5, 10, 25, of 50, fold compared to the level of expression in a standard (not provided the β-lactamase inhibitor), in at least some cases.

In particular embodiments of the disclosure, an individual is given an agent for a bacterial invention in addition to the one or more agents of the present invention including a β-lactamase inhibitor and a carbapenem. Such additional therapy may include antibiotics. When combination therapy is employed with an agent of the present invention, the additional therapy may be given prior to, at the same time as, and/or subsequent to the agent of the present invention.

Pharmaceutical Preparations

Pharmaceutical compositions of the present invention comprise an effective amount of one or more agents of the present invention, such as a β-lactamase inhibitor and a carbapenem, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one agent of the present invention or additional active ingredient will be known to those of skill in the art in light of the present disclosure, as exemplified by Remington: The Science and Practice of Pharmacy, $21^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The antibacterial agents of the present invention may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference). The antibacterial agents of the present invention may be provided to the individual in need thereof by dietary ingesting one or more comestibles that comprise the inducer, such as herbs, berries, and/or fruits.

The agents of the present invention including a β-lactamase inhibitor and a carbapenem described in this invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention, including the agents and pharmaceutical compositions including the agents, suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include one or more antibacterial agent of the present invention, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the compositons of the present invention may be dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In one embodiment of the present disclosure, the antibacterial agents of the present invention are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, antibacterial agents of the present invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,753,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the active compound or antibacterial agents of the present invention may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, an antibacterial agent (for example, a β-lactamase inhibitor and a carbapenem of the present invention) may be comprised in a kit.

The kits may comprise a suitably aliquoted of an antibacterial agent of the present invention and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the bacterial agent of the present invention and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The antibacterial agents of the present invention and composition(s) thereof may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

Examples of Chemical Structures

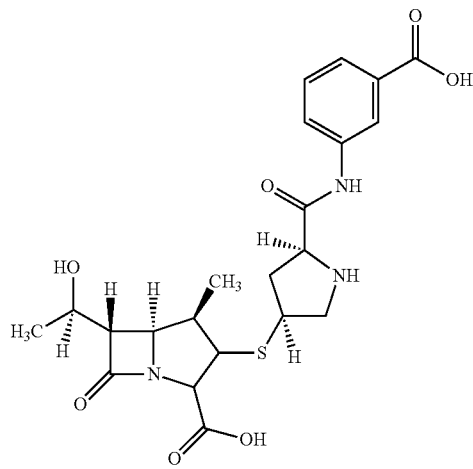

Ertapenem

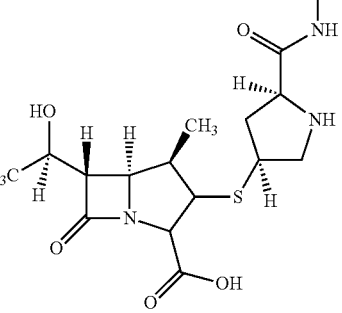

Meropenem

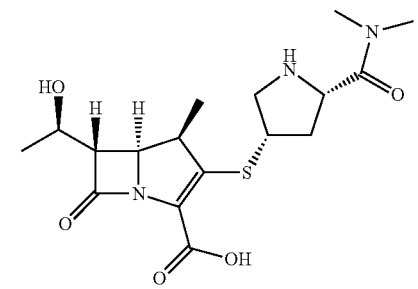

Imipenem

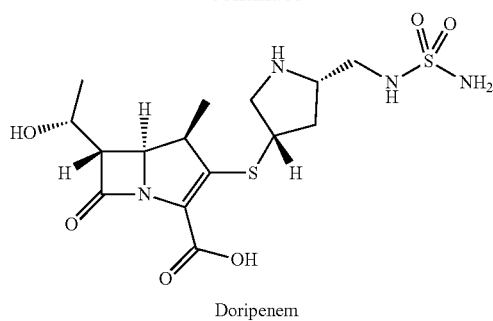

Doripenem

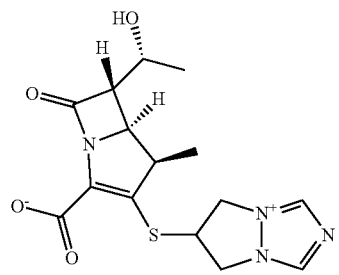

Biapenem

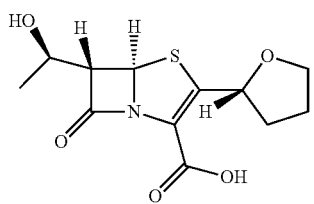

Faropenem

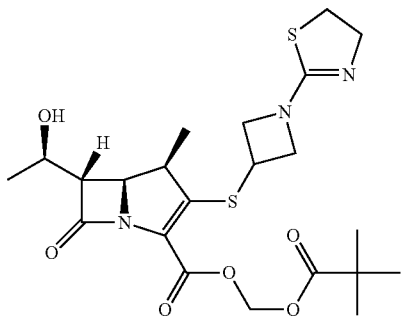

Tebipenem - pivoxil (a prodrug of tebipenem)

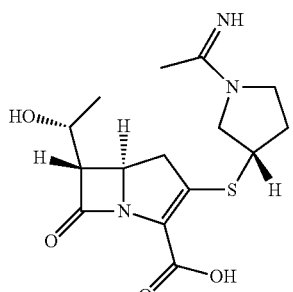

Panipenem

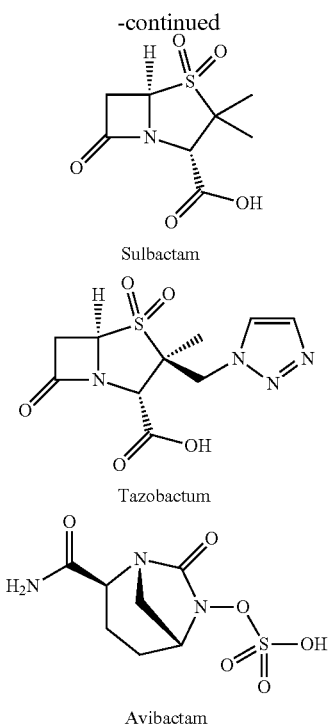

Sulbactam

Tazobactum

Avibactam

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating or preventing a mycobacteria infection in a subject in need thereof comprising administering an agent comprising avibactam and one or more carbapenem to the subject.

2. The method of claim 1 wherein the carbapenem is selected from the group consisting of ertapenem, meropenem, imipenem, doripenem, biapenem, faropenem, tebipenem, panipenem and a combination thereof.

3. The method of claim 1 wherein the treating or preventing of the mycobacteria infection occurs when at least one symptom of the mycobacteria infection is alleviated compared to a reference subject.

4. The method of claim 1 wherein the mycobacteria infection comprises *Mycobacterium abscessus*.

5. The method of claim 1 wherein the amount of avibactam is sufficient to reduce the minimum inhibitory concentration of the one or more carbapenem in the range of 2 to 32 fold.

6. The method of claim 1 wherein the amount of avibactam is sufficient to reduce the minimum inhibitory concentration of the one or more carbapenem by greater or equal to 2-fold.

7. The method of claim 1 wherein the amount of avibactam is sufficient to reduce the minimum inhibitory concentration of the one or more carbapenem by greater or equal to 3-fold.

8. The method of claim 1 wherein the amount of avibactam is sufficient to reduce the minimum inhibitory concentration of one or more carbapenem by greater or equal to 5-fold.

9. The method of claim 1 wherein the amount of avibactam is sufficient to reduce the minimum inhibitory concentration of one or more carbapenem by greater or equal to 8-fold.

10. The method of claim 1 wherein the amount of avibactam is sufficient to reduce the minimum inhibitory concentration of one or more carbapenem by greater or equal to 13-fold.

11. The method of claim 1 wherein the amount of avibactam is sufficient to reduce the minimum inhibitory concentration of one or more carbapenem by greater or equal to 38-fold.

12. The method of claim 1 wherein the one or more carbapenem is selected from the group consisting of doripenem, tebipenem, ertapenem, imipenem, and panipenem.

13. The method of claim 1 wherein the one or more carbapenem is doripenem.

* * * * *